United States Patent [19]

Baldwin et al.

[11] 4,061,021
[45] Dec. 6, 1977

[54] RECORDING SOIL PENETROMETER

[75] Inventors: William I. Baldwin; Wesley F. Buchele, both of Ames, Iowa

[73] Assignee: Iowa State University Research Foundation, Inc., Ames, Iowa

[21] Appl. No.: 763,572

[22] Filed: Jan. 28, 1977

[51] Int. Cl.$^2$ .............................................. G01N 3/40
[52] U.S. Cl. ..................................................... 73/84
[58] Field of Search ............................... 73/84, 81, 89

[56] References Cited

U.S. PATENT DOCUMENTS

| | | | |
|---|---|---|---|
| 2,130,751 | 9/1938 | Meer | 73/84 |
| 2,259,491 | 10/1941 | Roller | 73/89 |
| 3,552,194 | 1/1971 | Hawes | 73/84 |

*Primary Examiner*—Jerry W. Myracle
*Attorney, Agent, or Firm*—Zarley, McKee, Thomte, Voorhees & Sease

[57] ABSTRACT

A recording soil penetrometer comprising a frame having upper and lower ends with a penetration probe extending downwardly from the lower end of the frame for penetration of the ground. A handle is operatively yieldably vertically movably mounted on the upper end of the frame for forcing the probe downwardly into the ground. A recording drum is rotatably mounted, about a vertical axis, on the frame and is adapted to have pressure sensitive recording paper mounted thereon. A ground-engaging apparatus is vertically movably mounted on the lower end of the frame. A rubber foot is provided on the lower end of the ground-engaging apparatus for engagement with the ground. A scriber is mounted on the upper end of the ground-engaging apparatus which is adapted to scribe the recording paper on the recording drum. A force link apparatus operatively interconnects the handle and the recording drum for causing rotation of the drum relative to the force required to cause the probe to penetrate the soil. The scriber scribes a depth-penetration resistance graph on the recording paper as the probe penetrates the soil.

6 Claims, 4 Drawing Figures

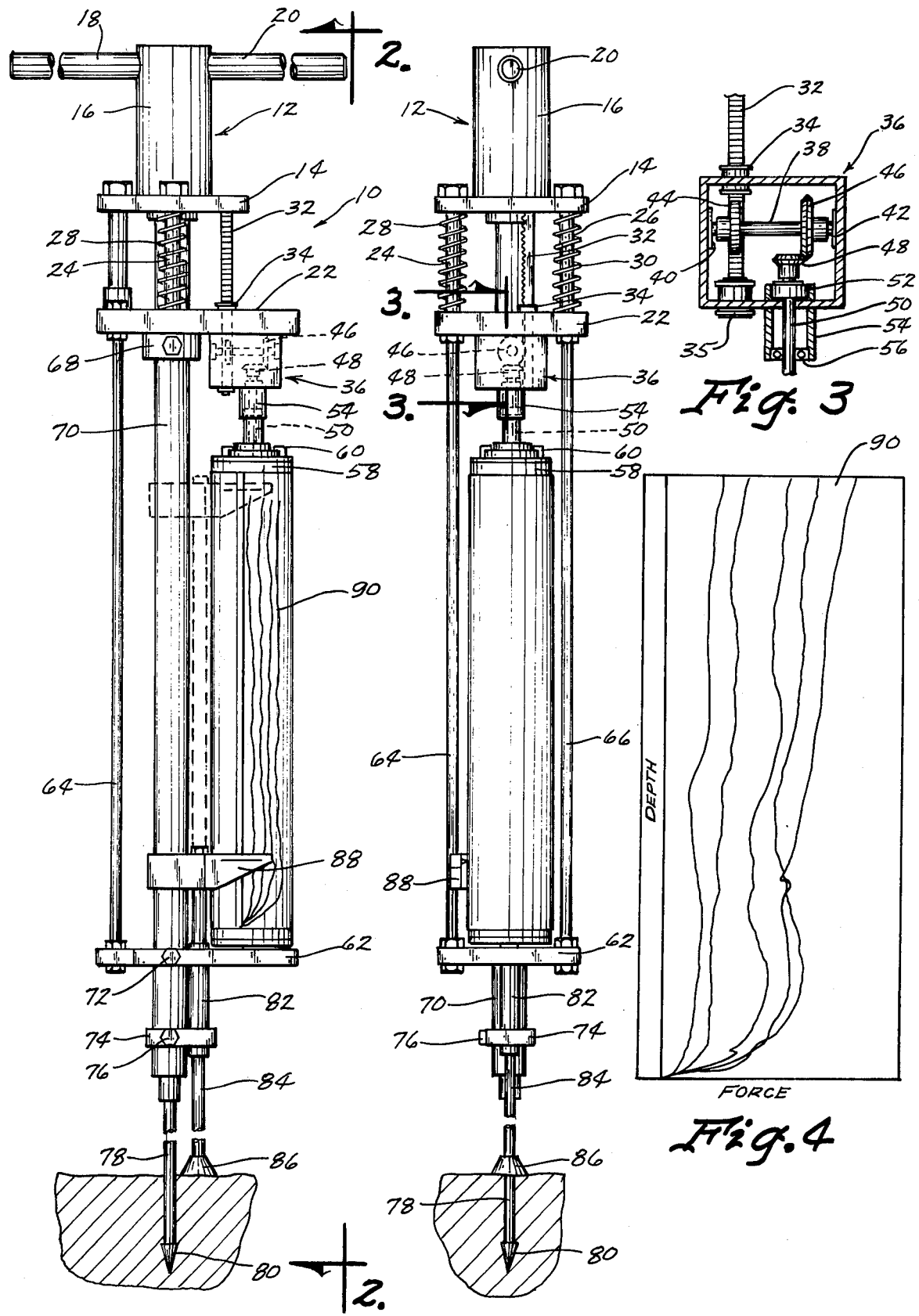

RECORDING SOIL PENETROMETER

BACKGROUND OF THE INVENTION

This invention relates to a penetrometer and more particularly to a recording soil penetrometer which provides a depth-penetration resistance graph as the penetrometer is forced into the ground.

Throughout history, man has used his senses to determine soil conditions. He could observe cracks and fissures caused by drying of the soil and could see the rocks, stones and organic material which made up the soil to obtain a visual impression of physical conditions of the soil. He estimated moisture content of the soil by compressing the soil in his hand. If his footprint was shallow, the soil was firm. If he sank in the soil to his knees, he knew the soil was soft. Though these were not exact methods, by trial and error, proper conditions for plant growth were estimated. These experiences were passed from generation to generation.

Various means for measuring soil conditions have been devised. Laboratory analysis of organic matter and nutrients, aggregate sizes, moisture content, biological activity, and shear strength provide knowledge about soil conditions. The penetrometer is one of the instruments used to measure mechanical properties of soil. A penetrometer such as described in ASAE Recommendation: ASAE R313.1 was developed and has been widely used by the Army Corps of Engineers and by highway contractors for a number of years. The size of cone tip used and penetration force can be translated into cone index which is related to penetrating resistance. The normal practice of using the conventional cone penetrometer involves one person pushing the penetrometer into the ground at a uniform rate and another person reading and recording force readings at each increment of depth. The discrete data is then plotted on graph paper to give a depth versus penetrating resistance graph. The described method of operation misses much of the information required by the researcher and results in a graph which is the average of questionable material.

Therefore, it is a principal object of the invention to provide a penetrometer which provides a depth-penetration resistance graph as the penetrometer is forced into the ground to increase the accuracy of the data.

A still further object of the invention is to provide a penetrometer which records all of the necessary required data.

A still further object of the invention is to provide a penetrometer which is portable.

A still further object of the invention is to provide a penetrometer which may be operated in an efficient manner.

A still further object of the invention is to provide a penetrometer which is simple both in construction and operation.

These and other objects will be apparent to those skilled in the art.

BRIEF DESCRIPTION OF THE DRAWINGS

FIG. 1 is a partial side elevational view of the penetrometer of this invention:

FIG. 2 is a view of the penetrometer of FIG. 1 as seen on lines 2—2 of FIG. 1:

FIG. 3 is a sectional view seen on lines 3—3 of FIG. 2; and

FIG. 4 depicts the graph which is provided by the apparatus.

SUMMARY OF THE INVENTION

A recording soil penetrometer is disclosed and includes a frame having a penetration probe extending downwardly from the lower end thereof adapted to penetrate the soil upon downward vertical force being applied thereto. A handle is yieldably vertically movably mounted on the upper end of the frame and is connected by means of a force link to a recording drum rotatably mounted on the frame. A rod is vertically movably mounted on the lower end of the frame and has a rubber foot at the lower end thereof which is adapted to engage the surface of the soil. A scriber is mounted on the upper end of the rod and is adapted to scribe the recording paper on the recording drum. The scriber scribes a depth-penetration resistance graph on the recording paper dependent upon the resistance offered by the soil and the depth of penetration.

DESCRIPTION OF THE PREFERRED EMBODIMENT

The penetrometer of this invention is referred to generally by the reference numeral 10. Penetrometer 10 comprises a handle 12 including a bottom plate 14, post 16 and transversely extending handle portions 18 and 20.

Handle 12 is connected to a plate-like frame 22 by means of bolts 24 and 26 extending therebetween. Bolts 24 and 26 are slidably received by bottom plate 14 and frame 22 with springs 28 and 30 embracing bolts 24 and 26 as indicated to yieldably maintain the bottom plate 14 and frame 22 in the spaced-apart relationship illustrated in the drawings.

Rack 32 is secured to bottom plate 14 and extends downwardly therefrom through frame 22 and through bearings 34 and 35 mounted on the upper and lower ends of a gear box 36. Shaft 38 is rotatably mounted in bearings 40 and 42 secured to gear box 36 and has gears 44 and 46 mounted thereon for rotation therewith. Gear 44 is in mesh with the teeth of rack 32. As seen in FIG. 3, gear 46 is in mesh with gear 48 which is mounted on the upper end of shaft 50 rotatably extending downwardly through bearing 52, bushing 54 and bearing 56. The lower end of shaft 50 is secured to the upper end of a rotatable recording drum 58 by an anti-shock and zero adjust coupling referred to generally by the reference numeral 60. The lower end of drum 58 is rotatably mounted on a plate-like frame 62. A pair of stabilizer rods 64 and 66 are secured to frames 22 and 62 and extend therebetween to maintain the frames in their spaced-apart condition seen in FIGS. 1 and 2.

Collar 68 is secured to the underside of frame 22 and has the upper end of rod 70 secured therein. Rod 70 extends through frame 62 and is secured thereto by bolts 72. Frame 74 is mounted on rod 70 adjacent the lower end thereof by bolts 76. Probe 78 is positioned on the lower end of rod 70 and extends downwardly therefrom to terminate in a penetrating cone 80.

Bushing 82 is secured to frame 62 and 64 by any convenient means and slidably receives a probe 84 which has a ground engaging foot portion 86 on the lower end thereof. The upper end of probe 84 has a scriber apparatus 88 mounted thereon for scribing the pressure sensitive paper 90 mounted on drum 58. Scriber apparatus 88 embraces rod 70 so as to be properly maintained in position relative to the recording paper and the drum.

In use, the pressure sensitive recording paper 90 is mounted on the recording drum 58 by any convenient means. The relative lengths of probe 78 and 84 are such that the scriber apparatus 88 will be positioned closely adjacent the lower end of the recording paper when the foot 86 and cone 80 are resting on the ground. The operator then applies downward force to the handles 18 and 20 to cause the cone 80 to penetrate the soil. The foot 86 does not penetrate the soil and maintains the scriber apparatus 88 stationary in height with respect to the soil surface throughout the sampling operation. If the cone 80 penetrates the soil without any resistance being experienced thereby, a straight vertical line would appear on the recording paper and such a straight vertical line would indicate the depth to which the cone penetrated the soil as well as the fact that no resistance was encountered. However, most soils will provide some resistance to the penetration of the cone 80 and such resistance will be experienced by the force link operatively connecting the handle to the drum. Downward force on the handle, to counteract the resistance experienced by the cone, will result in the springs 28 and 30 being compressed and will result in the rack 32 moving downwardly with the handle 12 relative to frame 22. Downward movement of rack 32 causes gear 34, shaft 38, gear 42, gear 48 and shaft 50 to be rotated relative to the penetration resistance. Rotation of shaft 50 causes the drum 58 and the recording paper thereon to be rotated about a vertical axis relative to the scriber apparatus so that an irregular line will appear on the recording paper.

After the probe or cone has been removed from the soil, the pressure-sensitive paper 90 is removed from the drum. The angular displacement (penetrating resistance), while on the drum, becomes the Y-axis (force) and is calibrated in pounds per square inch for a given spring rate and cone. The axial length, while on the drum, becomes the X-axis on the rectangular graph and is the depth reading.

It has been observed, when using the penetrometer of this invention, that an average of the soil of a given area could be rapidly determined by recording five readings on a single sheet of paper. An average line is then drawn through the five lines by hand. Since the pressure-sensitive paper is not graph paper, a graph template should be placed over the paper and the average readings read from the graph.

This method of sampling and recording soil strength has several advantages over the standard penetrometer which is comprised of a proving ring and a dial indicator in that the device of this invention provides a permanent record. Additionally, the penetrometer of this invention may be operated by a single person and the data is automatically recorded.

It has been found that the recording penetrometer of this invention is especially well suited for determining the effect of wheel traffic in the strength of tilled soil and the effect of tillage on the strength of soil. As in other penetrometers, strength of soil is related to the force and the size of the penetrating cone. The range of this instrument may be changed by adding or subtracting springs in the force link or by changing the size of the cone.

Thus, it can be seen that a novel penetrometer has been provided which accomplishes at least all of its stated objectives.

We claim:

1. A penetrometer comprising,
   a frame means having upper and lower ends,
   a probe means on the lower end of said frame means for penetrating the soil,
   ground engaging means vertically movably mounted on the lower end of said frame means,
   a handle means operatively yieldably vertically movably mounted on the upper end of said frame means,
   a recording drum means rotatably mounted, about a vertical axis, on said frame means and being adapted to have recording paper thereon,
   a scriber means operatively connected to said ground engaging means for scribing the recording paper,
   and means operatively interconnecting said handle means to said drum for causing rotation of said drum relative to the force required to cause said probe means to penetrate the soil,
   said scriber means scribing a depth-penetration resistance graph on the recording paper as said probe is penetrating the soil.

2. The penetrometer of claim 1 wherein said means interconnecting said handle means to drum comprises a force link means.

3. The penetrometer of claim 2 wherein said force link means comprises a spring means extending between said handle means and said frame means, and means connecting said handle means to said drum for converting vertical movement of said handle means, relative to said frame means, to corresponding rotational movement of said drum.

4. The penetrometer of claim 3 wherein said means comprises a toothed rack secured to said handle means and extending downwardly therefrom, a horizontally disposed rotatable shaft mounted on said frame means, a first gear on said shaft for rotation therewith and being in mesh with said toothed rack, a second gear on said shaft for rotation therewith, said drum having a vertically disposed rotatable shaft extending upwardly from its center longitudinal axis, a third gear on said drum shaft in mesh with said second gear.

5. The penetrometer of claim 1 wherein a foot means is provided on the lower end of said ground engaging means for preventing said ground engaging means from penetrating the soil.

6. The penetrometer of claim 1 wherein said probe has a penetrometer cone on its lower end.

* * * * *